though the contaminated liquid with silica. For example, boron
United States Patent [19]
Vogel et al.

[11] 4,433,197
[45] Feb. 21, 1984

[54] REMOVING BORON TRIFLUORIDE FROM COORDINATION COMPOUND CONTAMINANTS IN ORGANIC LIQUIDS

[75] Inventors: Roger F. Vogel, Jefferson Township, Butler County, Pa.; Ajay M. Madgavkar, Irvine, Calif.; Harold E. Swift, Gibsonia, Pa.

[73] Assignee: Gulf Research & Development Company, Pittsburgh, Pa.

[21] Appl. No.: 396,256

[22] Filed: Jul. 8, 1982

[51] Int. Cl.³ ............................ C07C 7/12; C07C 3/18
[52] U.S. Cl. ..................................... 585/823; 208/262; 208/291; 585/465; 585/472; 585/726; 585/824; 585/525; 585/830
[58] Field of Search .............. 585/465, 472, 473, 525, 585/726, 823, 824, 830, 712; 208/262, 291

[56] References Cited
U.S. PATENT DOCUMENTS

| | | | |
|---|---|---|---|
| 2,347,945 | 5/1944 | Frey | 585/823 |
| 3,200,163 | 8/1965 | Fenske | 585/823 |
| 4,213,001 | 7/1980 | Madgavkar et al. | 585/525 |
| 4,308,414 | 12/1981 | Madgavkar et al. | 585/525 |
| 4,365,105 | 12/1982 | Morganson et al. | 585/525 |

*Primary Examiner*—Delbert E. Gantz
*Assistant Examiner*—A. Pal
*Attorney, Agent, or Firm*—Deane E. Keith; Forrest D. Stine; Donald L. Rose

[57] ABSTRACT

Boron trifluoride is removed from coordination compounds contaminating organic liquids by contacting the contaminated liquid with silica. For example, boron trifluoride is removed from a boron trifluoride-n-butanol coordination compound contaminating a 1-olefin oligomer product by passing the contaminated liquid oligomer through a bed of silica.

8 Claims, No Drawings

REMOVING BORON TRIFLUORIDE FROM COORDINATION COMPOUND CONTAMINANTS IN ORGANIC LIQUIDS

SUMMARY OF THE INVENTION

Boron trifluoride contaminant which is coordinated with a polar compound and is present in minor amounts in an organic liquid is removed from the coordination compound and the organic liquid by contacting the organic liquid with particulate silica.

DESCRIPTION OF THE INVENTION

Coordination compounds of boron trifluoride and a polar compound are used as catalysts in relatively small amounts in the synthesis of a wide variety of liquid organic compounds, in particular liquid hydrocarbon compounds, including use as a catalyst in polymerizations, in alkylations, in esterifications, and the like. The soluble boron trifluoride coordination compound catalyst is in the reaction liquid during the reaction. Once the catalyzed reaction is completed, this minor amount of boron trifluoride must be removed from the liquid organic product solution. But this removal presents costly processing and disposal problems.

These problems can be exemplified by the process in current use for the preparation of synthetic hydrocarbon functional fluids, such as synthetic lubricating oils, from higher 1-olefins, particularly 1-decene. In the process, as described in U.S. Pat. No. 4,045,507 for one, the 1-decene is oligomerized to a product predominating in the trimer and tetramer in a reactor pressurized with boron trifluoride and containing a coordination compound formed from boron trifluoride and a suitable polar compound such as n-butanol. The resulting oligomer product solution will contain the boron trifluoride, which must be separated from the product.

A typical processing scheme frequently recommended for eliminating boron trifluoride from the oligomer product includes the chemical destruction of the boron trifluoride by the addition of an aqueous caustic wash stream. But this procedure involves the loss of the relatively expensive boron trifluoride and further involves rather costly by-product handling and disposal procedures to avoid environmental contamination. The process also requires the removal of the introduced moisture from the hydrocarbon product. Furthermore, the n-butanol contaminant in the product must be separately removed and treated.

We have discovered a relatively inexpensive method for removing boron trifluoride which is tied up in a coordination compound that is dissolved in an organic liquid. Our process is particularly beneficial, both for economical and for environmental reasons, because the separated boron trifluoride is recovered intact and can be readily reused. As a result, both the boron trifluoride costs and the overall processing costs are substantially reduced. Additionally, any current environmental problems involving catalyst by-product waste disposal are substantially eliminated by our process.

The boron trifluoride can be coordinated with a suitable polar compound in situ or it can be added to the reactor as the pre-reacted coordination compound. When the reactor is pressured with boron trifluoride in the presence of the coordinating polar compound, both dissolved, uncomplexed boron trifluoride and complexed boron trifluoride will be present in the reaction liquid. Various organic polar compounds have been recommended as useful for forming coordination compounds with boron trifluoride for use as a catalyst. These include: aliphatic ethers, such as dimethyl ether and diethyl ether; aliphatic alcohols, such as methanol, ethanol, n-butanol and decanol; polyols, such as ethylene glycol and glycerol; aliphatic carboxylic acids, such as acetic acid, propanoic acid and butyric acid; esters, such as ethyl acetate and methyl propionate; ketones, such as acetone; aldehydes, such as acetaldehyde and benzaldehyde and acid anhydrides, such as acetic acid anhydride and succinic acid anhydride.

The product from the boron trifluoride-catalyzed process, whether batch or continuous, will contain the minor, catalytic amount of the boron trifluoride-coordination compound catalyst. This boron trifluoride must be removed following reaction since it inherently contaminates the product. In general, it is desired that every product which is synthesized using boron trifluoride catalyst be essentially free of this substance. Although boron trifluoride-containing coordination-compound contaminants in organic liquids are generally present because of a catalyst function, our boron trifluoride removal process is suitable whether or not the contaminating boron trifluoride had served as a catalyst. In general, boron trifluoride contaminant can be effectively removed from organic liquids by our process when it is present in an amount as high as about five to ten weight percent. More generally, boron trifluoride contaminant will be present in organic liquids in an amount between about 0.005 and about one percent.

The silica composition which we use in our process for removal of the boron trifluoride is present in particulate form, generally within a size range of between about 10 mm and about 400 mesh, and preferably within a range of about 10 and about 100 mesh. In using the expression "silica composition", we mean to include not only silica itself but also silica-aluminas comprising at least about 50 mol percent silica. A particularly fortuitous and advantageous discovery by us was that the silica removes boron trifluoride from its coordination compound with a polar compound, leaving the polar compound in the organic product liquid. We have determined that silica is an effective adsorbent up to its saturation point for boron trifluoride.

Our process for removing from trifluoride contaminant from organic liquids can be conveniently carried out at room temperature (20°–25° C.) or lower, such as about 0° C. Since elevated temperatures prevent the adsorption of the boron trifluoride by the silica, a temperature of about 100° C. is generally not exceeded in the adsorption process, and much lower temperatures are preferred, such as a maximum temperature of about 75° C.

In our adsorption process the organic liquid can suitably be passed through the bed of silica at a weight hourly space velocity in the range of about 0.1 to about 100 hr.$^{-1}$, preferably about 0.5 to about 20 hr.$^{-1}$, and most preferably about 1 to about 5 hr.$^{-1}$.

When the silica adsorbent is saturated with boron trifluoride, it is taken out of service. Desirably, the boron trifluoride is recovered from this adsorbent by extracting it, and both the boron trifluoride and the adsorbent are reused. In a convenient procedure for the recovery of the boron trifluoride, the silica is heated at a moderate temperature, such as about 100° C. at a reduced pressure, to vaporize off the boron trifluoride. This recovered boron trifluoride can then be directly reused in the process. Alternatively, the boron trifluoride can be stripped from the silica adsorbent by contacting it with a polar compound. In this stripping procedure, the concentration of the polar compound will be high relative to the boron trifluoride. This recovery of boron trifluoride from the sorbent is possible because, it is believed, the distribution of the boron trifluoride between the phases is governed by equilibrium. For process simplification, the polar compound used in this recovery stage is the same one used in the coordination compound catalyst.

DESCRIPTION OF PREFERRED EMBODIMENTS

EXAMPLE 1

Davison Grade 59 silica of 40/50 mesh size was used in the following experiment. A liquid synthetic hydrocarbon oligomer mixture was produced from 1-decane by the process described in U.S. Pat. No. 4,045,507 using a boron trifluoride-n-butanol complex in a system pressured with boron trifluoride gas. The oligomer product mixture was contaminated with 0.482 percent boron trifluoride, 62.4 percent of which was coordinated with n-butanol and 37.6 percent of which was free boron trifluoride dissolved in the product mixture.

A 1.212 gm. quantity of the silica adsorbent was placed in a glass column to form a bed about one-half inch in diameter and 1.5 inches high. The boron trifluoride-contaminated oligomer mixture was pumped from a continuously stirred reactor through the adsorbent at a weight hourly space velocity of 63 hr.$^{-1}$ and at a temperature of 20°–25° C. Samples of decontaminated product were collected and were analyzed for boron using an atomic adsorption technique. The results, including the percent removal of the boron trifluoride by the silica, are shown in Table I.

TABLE I

| Sample | Total amount collected, gms | B in treated product, ppm | Total BF$_3$ removed, % |
|---|---|---|---|
| 1 | 121.9 | 13 | 98.3 |
| 2 | 152.3 | 20 | 97.4 |
| 3 | 182.8 | 32 | 95.8 |
| 4 | 198.1 | 32 | 95.8 |

From these data it can be determined that 1.212 g. of silica removed 0.915 g of boron trifluoride from 198.1 g. of contaminated oligomer without showing any sign of having reached its adsorption capacity. Since the contaminated product prior to the silica adsorption treatment was determined, by analysis, to contain 3,280 ppm n-butanol, the 198.1 gms. of contaminated product, before treatment, contained 0.65 gm. of n-butanol. The silica was analyzed after treatment, and only 0.043 mg. of n-butanol was found on the silica.

EXAMPLE 2

In another experiment, a 2 g. sample of the silica adsorbent was subjected to five cycles of adsorption and regeneration using n-butanol to rinse the adsorbed boron trifluoride from the silica. In each cycle, the silica was agitated with 70 ml. of crude oligomer product for one hour to remove the boron trifluoride from the product liquid. After separating out the silica, the boron trifluoride was rinsed from the silica by agitation with 35 ml. of n-butanol. At the end of the fifth cycle, a 24.3 g mixture of the recovered boron trifluoride in an excess of the n-butanol with which it was rinsed from the silica was used in the batch oligomerization of 15 g of 1-decene. This reaction mixture, containing 0.2 percent boron trifluoride, was agitated in a 100 cc reactor at 70° C. for one hour under a nitrogen atmosphere. Notwithstanding the fact that there was a large excess of the n-butanol in the reaction mixture compared with the boron trifluoride, there was 18.5 percent oligomerization to a product containing 28.2 percent dimer, 51.3 percent trimer, 16.4 percent tetramer, and 4 percent pentamer.

It is to be understood that the above disclosure is by way of specific example and that numerous modifications and variations are available to those of ordinary skill in the art without departing from the true spirit and scope of the invention.

What is claimed as the invention is:

1. A method for removing boron trifluoride from a coordination compound of boron trifluoride and an organic polar compound present as a minor contaminant in a hydrocarbon liquid which comprises contacting a particulate silica composition with a hydrocarbon liquid contaminated with said coordination compound of boron trifluoride and an organic polar compound whereby the boron trifluoride is separated from said organic polar compound out of the coordination compound and out of the hydrocarbon liquid by the silica and said separated organic polar compound remains in the hydrocarbon liquid.

2. A method for removing boron trifluoride from a coordination compound contaminant in a hydrocabon liquid in accordance with claim 1 in which the hydrocarbon liquid contains up to about 10 percent boron trifluoride.

3. A method for removing boron trifluoride from a coordination compound contaminant in a hydrocarbon liquid in accordance with claim 1 in which the silica is of a particle size between about 10 mm and about 400 mesh.

4. A method for removing boron trifluoride from a coordination compound contaminant in a hydrocarbon liquid in accordance with claim 1 in which the temperature is between about 0° C. and about 100° C.

5. A method for removing boron trifluoride from a coordination compound contaminant in a hydrocarbon liquid in accordance with claim 1 in which the decontaminated hydrocarbon liquid is substantially completely freed of boron trifluoride.

6. A method for removing boron trifluoride from a coordination compound comtaminant in a hydrocarbon liquid in accordance with claim 1 in which the organic polar compound is an alkyl alcohol having from one to about ten carbon atoms.

7. A method for removing boron trifluoride from a coordination compound contaminant in a hydrocarbon liquid in accordance with claim 1 in which the organic polar compound is n-butanol.

8. A method for removing boron trifluoride from a coordination compound comtaminant in a hydrocarbon liquid in accordance with claim 1 in which said organic polar compound is an oxygen-containing organic polar compound.

* * * * *